(12) United States Patent
Wilke et al.

(10) Patent No.: US 7,651,946 B2
(45) Date of Patent: Jan. 26, 2010

(54) WET ETCH PROCESSING (75) Inventors: Nicolle Wilke, Reutlingen (DE);
Anthony Morrissey, County Cork (IE)

(73) Assignee: University College Cork - National University of Ireland, Cork, Cork (IE)

( * ) Notice: Subject to any disclaimer, the term of this patent is extended or adjusted under 35 U.S.C. 154(b) by 429 days.

(21) Appl. No.: 11/637,020

(22) Filed: Dec. 12, 2006

(65) Prior Publication Data

US 2007/0134829 A1 Jun. 14, 2007

Related U.S. Application Data (60) Provisional application No. 60/749,086, filed on Dec. 12, 2005.

(51) Int. Cl.
*H01L 21/311* (2006.01)
(52) U.S. Cl. .................. 438/701; 438/40; 438/43; 438/640; 438/713
(58) Field of Classification Search ............. 438/44–43, 438/640–673, 700–702, 713
See application file for complete search history.

(56) References Cited

U.S. PATENT DOCUMENTS 5,855,801 A 1/1999 Lin et al. ............... 216/2
6,096,656 A * 8/2000 Matzke et al. ............. 438/702
6,312,612 B1 11/2001 Sherman et al. .............. 216/2

* cited by examiner

*Primary Examiner*—Dung A. Le
(74) *Attorney, Agent, or Firm*—Jacobson Holman PLLC (57) ABSTRACT A method of wet etching produces high-precision microneedle arrays for use in medical applications. The method achieves precise process control over microneedle fabrication, at single wafer or batch-level, using wet etching of silicon with potassium hydroxide (KOH) solution by accurately identifying the etch time endpoint. Hence, microneedles of an exactly required height, shape, sharpness and surface quality are achieved. The outcome is a reliable, reproducible, robust and relatively inexpensive microneedle fabrication process. Microneedles formed by KOH wet etching have extremely smooth surfaces and exhibit superior mechanical and structural robustness to their dry etched counterparts. These properties afford extra reliability to such silicon microneedles, making them ideal for medical applications. The needles can also be hollowed. Wet etched silicon microneedles can then be employed as masters to replicate the improved surface and structural properties in other materials (such as polymers) by moulding.

32 Claims, 10 Drawing Sheets

NeedleSoft Development Center - Design and Process Documentation of Silicon Microneedles Nomenclature | Calibration Mask | Calibration Process | Mask Design | Process Documentation | Needle Geometry | About

Mask Design

INPUT
- Needle height hn [µm]: 300
- Width on top w2 [µm]: 50
- Chip size [mm²]: 10 x 5

[Calculate output design parameters]

OUTPUT

Standard Square Mask
- Square length [µm]:
- Gap width [µm]:
- Needle density (chip) [µm]:
- No of needles: ☐ x ☐

Square Mask with Beams
- Square length [µm]:
- Beam width [µm]:
- Gap width [µm]:
- Needle density (chip) [µm]:
- No of needles: ☐ x ☐

---

NeedleSoft Development Center - Design and Process Documentation of Silicon Microneedles Nomenclature | Calibration Mask | Calibration Process | Mask Design | Process Documentation | Needle Geometry | About

Mask Design

INPUT
- Needle height hn [µm]: 300.
- Width on top w2 [µm]: 50
- Chip size [mm²]: 10 x 5

[Calculate output design parameters]

OUTPUT

Standard Square Mask
- Square length [µm]: 650
- Gap width [µm]: 76
- Needle density (chip) [µm]: 78
- No of needles: 13 x 6

Square Mask with Beams
- Square length [µm]:
- Beam width [µm]:
- Gap width [µm]:
- Needle density (chip) [µm]:
- No of needles: ☐ x ☐

WET ETCH PROCESSING

This is a complete application claiming the benefit of U.S. provisional application No. 60/749,086, filed Dec. 12, 2005.

FIELD OF THE INVENTION

The invention relates to manufacture of microstructure needles ("microneedles") from materials such as silicon.

PRIOR ART DISCUSSION

It is known to fabricate silicon microneedles by dry etching technologies using various gas compositions and processes. A large variety of needle structures, both solid and hollow, are possible by appropriate mask and process design in dry etching. However, dry etching processes are expensive, and the process does suffer from some drawbacks including for example the requirement for specialised equipment operated by highly trained personnel. Also, batch processing is generally not possible as usually only one wafer can be treated at a time.

U.S. Pat. No. 5,855,801 describes a wet etch process using hydrofluoric acid for fabricating microneedles by providing a substrate, depositing an unetchable membrane over the substrate, and opening etching holes in the membrane layer to allow flow of etchant underneath to form a cavity and provide a desired needle shape.

The invention is directed towards providing an improved process for fabricating microstructures.

SUMMARY OF THE INVENTION

According to the invention, there is provided a process for manufacturing a microstructure needle article having a stem and a tip, the process comprising the steps of:
  providing a semiconductor bulk material,
  applying a mask to the bulk material, the mask having openings,
  exposing the pattern-masked bulk material to an hydroxide liquid etchant,
  allowing the hydroxide liquid etchant to enter the mask openings and to etch the bulk material until a desired out-of-plane needle shape is achieved, in which the needle tip is under, and pointing towards, the mask;
  wherein the process comprises the step of predicting remaining etch time by monitoring dimensions of the bulk material during etching, calculating actual etch rates in particular directions, and using said calculations to predict the remaining etch time until a stop time.

In one embodiment, the monitoring is performed to recognise a transition from one etching stage to a next etching stage.

In one embodiment, the monitoring is performed to recognise a transition from one etching stage to a next etching stage; and wherein etch rates for particular crystal planes for each stage are calculated.

In one embodiment, the prediction step comprises predicting:
  (a) a time $t_1$ for etching to a base of the needle; and
  (b) a time $t_2$ for etching to the tip of the needle In one embodiment, the monitoring steps comprise taking measurements a plurality of times close to the end of the etching.

In one embodiment, the monitoring steps comprise taking measurements a plurality of times close to the end of the etching; and wherein the etching is temporarily stopped while the monitoring takes place.

In one embodiment, the prediction step calculates a plurality of different etch rates.

In one embodiment, the prediction step predicts the stop time as being when bulk material crystal planes will intersect under the mask to form the needle tip.

In one embodiment, the prediction step predicts the stop time as being when the crystal planes will intersect under the mask to form the needle tip; and wherein the end point is when the mask will detach.

In another embodiment, the prediction step predicts the stop time as being when the crystal planes will intersect under the mask to form a point; and wherein eight planes intersect at the stop time.

In one embodiment, the prediction step predicts a stop time as being when crystal planes will intersect under the mask to form a point; and wherein the end point is when the mask will detach; and wherein eight planes intersect at the stop time.

In a further embodiment, the prediction step predicts the stop time as being when crystal planes will intersect under the mask to form a point; and wherein eight planes intersect at the stop time; and wherein said planes are {312} planes.

In one embodiment, the prediction step predicts the stop time as being when crystal planes will intersect under the mask to form a point; and wherein the article base has {121} crystal planes.

In one embodiments, the prediction step predicts when certain crystal planes will be removed.

In one embodiment, the prediction step predicts different etching rates for different dimensions.

In one embodiment, the prediction step predicts different etching rates for different dimensions; and predicts a different etching rate in the top width of the needle frustum than diagonal width of the base.

In one embodiment, the prediction step predicts different etching rates for different dimensions; and predicts a different etching rate in the top width of the needle frustum than diagonal width of the base; and wherein the process simultaneously fabricates an array of upright out-of-plane needles.

In one embodiment, the prediction step predicts different reduction rates for different dimensions; and predicts a different etching rate in the top width of the needle frustum than diagonal width of the base; and wherein the process simultaneously fabricates an array of upright out-of-plane needles; and wherein the process simultaneously fabricates a plurality of arrays of needles.

In one embodiment, the monitoring step is performed with only a subset of the arrays.

In one embodiment, the prediction step predicts different reduction rates for different dimensions; and predicts a different etching rate in the top width of the needle frustum than diagonal width of the base; and wherein the process simultaneously fabricates an array of upright out-of-plane needles; and wherein the process simultaneously fabricates a plurality of arrays of needles; and wherein the plurality of needles are fabricated on a semiconductor wafer.

In one embodiment, the prediction step predicts etch time according to predicted changes in crystal plane indices.

In one embodiment, the method comprises the further step of automatically generating an etch mask design according to target needle parameters, etch parameters, and predicted etch rates.

In one embodiment, the method comprises the further steps of using the microstructure needle as a master to produce a plurality of microstructure needles in a polymer material.

In one embodiment, the method comprises the further steps of using the microstructure needle as a master to produce a plurality of microstructure needles in a polymer material; and wherein the semiconductor needle is used as a master in a mould.

In one embodiment, the method comprises the further steps of creating a hollow in the microstructure needle.

In one embodiment, the mask is of nitride material.

In one embodiment, the mask openings are formed by plasma etching.

In one embodiment, the etchant is potassium hydroxide.

In one embodiment, the etchant temperature is above 70° C.

In one embodiment, the etchant temperature is approximately 79° C. and the etchant is potassium hydroxide.

In another aspect, the invention provides a process controller comprising a processor and an input interface, the input interface being for receiving process conditions and the processor being for performing any prediction step defined above.

The invention also provides a computer readable medium comprising software for performing any prediction step defined above when executing on a digital processor.

DETAILED DESCRIPTION OF THE INVENTION

Brief Description of the Drawings

The invention will be more clearly understood from the following description of some embodiments thereof, given by way of example only with reference to the accompanying drawings in which.

DESCRIPTION OF THE EMBODIMENTS

A method based on wet etching produces high-precision microneedles in an upright, out-of-plane, "bed of nails" array (or single needle) configuration for applications including, but not limited to, medical devices. The description below describes fabrication of solid needles, however, with appropriate mask design the needles may be hollow. In such case, solid microneedles are fabricated by the wet etch process described below, and then the capillaries are etched (for example by dry etching) into the backside of the needles to render them hollow. Uses of microneedle devices for medical applications are described, for example, in U.S. Pat. No. 6,312,612.

The method achieves precise process control over microneedle fabrication using wet etching of a semiconductor such as silicon in an alkaline solution. It achieves accurate prediction of the etch time endpoint, so that microneedles of an exactly required height, shape, sharpness and surface quality are achieved. The process is implemented in a batch, the batch including for example up to 25 wafers, each having for example 100 chips, and each chip having for example 100 microneedles in an array. One chip is used for example in a medical device for drug delivery among other biomedical applications. Because the process can be implemented in a batch there is excellent efficiency, in terms of reduction of processing time, costs and equipment requirements.

Also, because of the manner in which the wet etching timing is controlled, there is very precise control over microneedle dimensions. Because wet etching with alkaline media etches substrates such as silicon along its crystal plane, the resultant microstructures, such as the microneedles, are extremely robust and have smooth surfaces. It is well known that dry etching of silicon microneedles produces a brittle structure which is subject to deformation or breakage when subjected to stresses such as those experienced by the needles when the device is used in medical applications involving insertion into biological tissue. The smooth defect-free surface produced by wet etching, and the robust structure obtained, contribute to the structural and mechanical stability of the wet etched microneedles. Smooth surfaces are themselves also highly advantageous for the medical device applications, as the problem of removal of skin cells is avoided, and hence there is a much improved confidence in the extent of drug delivery. This is particularly important in the example of delivering for example vaccines to specific cell regions within the skin. Dry etched needles have a roughened surface which needs smoothening by additional post-fabrication processing in order to reduce needle occlusion by tissue/debris. The smooth wet etched needles of our process do not retain tissue on their surfaces on withdrawal from skin or other target tissue after insertion into same.

The etchant is preferably an alkaline solution, preferably a hydroxide, and most preferably potassium hydroxide. Such an etchant is very aggressive and hence, the etching extent (time) has heretofore been difficult to accurately control in order to achieve the microstructures of the desired dimensions, particularly height. Therefore such an etchant has not been successfully used heretofore to the knowledge of the inventors to achieve reliable and reproducible fabrication of microstructures such as microneedles of accurately controlled height. The invention overcomes this problem by the manner in which etching is controlled. That control is based on an in-depth analysis we have performed of the etching behaviour across the many involved crystal planes in the substrate, which is for example silicon. This understanding has led to our deriving of the mathematical equations which describe this etching process behaviour in terms of the etch rates across these various crystal planes.

Figure 1:
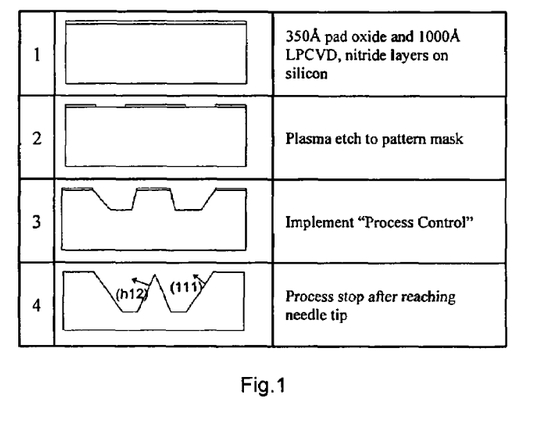
FIG. 1 is a flow diagram of a wet etch process flow of the invention to fabricate microneedle arrays.

Microneedles can then be replicated in other materials (such as, but not limited to, polymers) using moulding or embossing replication processes in which the silicon microneedle array is a master. Therein, the above-described improved surface and structural properties and qualities realised by wet etching, for example of silicon microneedles, is retained and reproduced in the polymer substrate. Referring to FIG. 1, the wet etch process for manufacturing microneedles is shown. Taking the example of fabricating microneedle arrays in silicon, in a first stage, nitride layers are formed on silicon following a number of photolithographic steps and sequences. In a second stage, there is plasma etching to pattern the nitride mask layer. In a third stage, wet etching in the alkaline solution, for example hot potassium hydroxide (KOH) proceeds until a process stopping point when a needle tip is correctly formed as desired. The third stage is stopped to take key dimensional measurements (see FIG. 2), data is inputted into NeedleSoft (FIGS. 9 to 18), and the latter outputs the remaining etching time. The etchant is extremely aggressive (high temperature concentrated alkaline solution), the silicon crystal planes are constantly changing as the needle is closer to being formed, and etching undercut (of the masking layer) progresses with often swift changes in etch rates across such crystal plane directions. Hence, in the process of the invention, the first NeedleSoft output is taken as a close approximation to the endpoint. The process is again stopped nearer this predicted time point, and the same measurements taken, to add to the accuracy of the endpoint identification. If the process is further stopped a third time, this will lead to even greater confidence in accuracy endpoint identification. We have achieved precise control with just one stop and with two stops, but as each stop takes only a matter of minutes, three stops are recommended for even more confidence in accuracy to the nearest minute. Such confidence is important because of the small dimensions. In one example, a 300 μm tall needle array which can take over 5 hours of etching, not including bath preparation and bath warm-up time, is desired. Without process control and knowledge of when to terminate the process, a user would quite easily over-etch, i.e. expose the silicon wafer to the KOH solution for an excessive period of time. To further highlight the need for accurate endpoint time identification, if this over-etching proceeds (at the end of the 5 hours of etching required in this example) for just a matter of some minutes, up to 20% or more of the intended needle height is lost and the reproducibility across an array and across the wafer is severely compromised. At each intermediate stopping stage (with increasing accuracy depending on number of stops), the two measurements taken are inserted into the user-friendly graphic user interface (GUI) on NeedleSoft (as shown in FIGS. 9 to 18 and described below) and the software determines how much etch time remains. The etching stage (stage 3) can then proceed to the indicated time endpoint, and the result will be an array of accurately predicted and achieved needle height, with wafer-level uniformity and batch-level uniformity which is completely reproducible and reliable.

Referring again to FIG. 1, a standard P-type silicon wafer with (100) orientation and crystal alignment marks was used in an example of the process. In this example, the first process stage is the deposition of a nitride layer on an oxide layer using for example Low Pressure Chemical Vapour Deposition (LPCVD) (stage 1). The oxide and nitride layers were lithographically patterned into square etch masks using a plasma etch process (stage 2). The patterned silicon wafer was etched using, in this example, a 29% w/v KOH solution at a temperature of 79° C. (more generally preferably greater than 70° C.) in a water-based bath with constant agitation. Our process and its process control are independent of bath composition and conditions.

Figure 3:
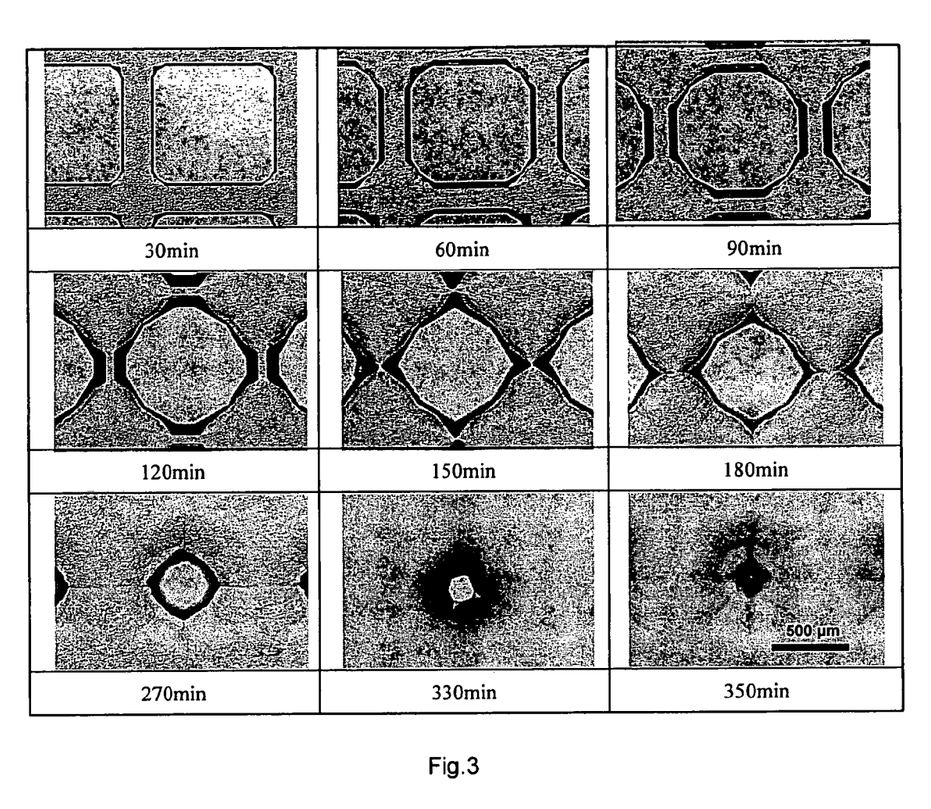
FIG. 3 is a set of micrographs showing the evolution of an etch process, for a single needle within an array, from an overhead view taken at various time intervals; observed is the disintegration of the masking layer in a controlled progression towards a single point, the realisation of a microneedle.

In one example of the process, the entire etch process was documented with optical microscopy (images and measurements) at time intervals throughout the etching stage (stage 3 in FIG. 1). These are shown in FIG. 3. Microneedles were also observed with Scanning Electron Microscopy (SEM). Comparisons of optical microscope and SEM measurements showed that optical microscopy is sufficiently accurate for our investigations, when the user is shown what to do and what to measure. This is another major benefit of our process control methodology. Optical microscopy allows a fast process control and time-efficient measurements for a large number of wafers, each with a large number of needle arrays, noting also that only one wafer from the batch needs to be removed for such intermediate examination. In fact, the needle geometry can be completely specified using only four measurements from the optical microscope, if a user or researcher wanted to acquire a complete in-depth analysis of any etching fabrication run.

Figure 2:
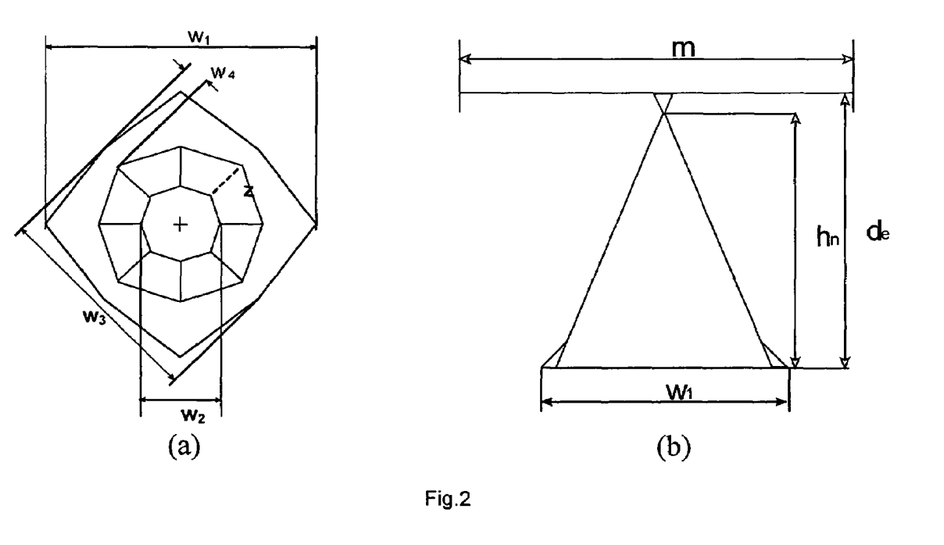
FIG. 2 shows diagrams of dimensions of microneedles.

FIG. 2 illustrates our nomenclature for the microneedle dimensions. In the plan view, FIG. 2(a), $w_1$ is the diagonal width of the bottom square in the [011] direction; $w_2$ is the width on top of the frustum in the [011] direction; and $w_3$ is the diagonal length at the bottom of the frustum in the [010] direction. The dimension $w_4$ is the distance between the crystal planes of the needle base (which appears as a rotated square when viewed from the top) and the high index crystal plane, which forms the needle sidewall. The Miller index h of the crystal planes is given by the aspect ratio of needle height to radius of outer circumcircle of the octagon and is denoted the "high index". For a sharp needle tip, h is given by:

$$h = \frac{h_n - \sqrt{2} \cdot w_4}{\left[\frac{w_3}{2} - w_4\right] \cdot \cos 22.5°} \quad (1)$$

If the distance $w_4$ is respectively large ($\geq 50$ μm), the needle height is not equal to the height of the high index crystal planes. In the side view, FIG. 2(b), $d_e$ is the total etch depth, and $h_n$ is the height of a microneedle formed from a mask (individual pad on the mask for that microneedle) of width m. The needle height $h_n$ is reduced from $d_e$ by $r_2$; this reduction being due to a small re-entrant structure with negatively sloped sidewalls (shown in FIG. 8). The distance from the mask corners to the needle tip is reduced by $r_2$, caused by the negative slope as well.

Etching Characteristics

FIG. 3 shows top-down micrographs of the evolution of a microneedle through convex corner undercutting of a square mask. In the case of the bath composition and conditions for this example (given above), the measured etch rate in the [100] direction was ca. 0.9 μm/min. FIG. 3, after 30 minutes, shows the emergence of {111}-silicon crystal planes as the long edges of the square masks are slowly underetched. The formation of {111} crystal planes on every edge of the square causes an increase of the bottom width. In addition, two types of crystal planes are observed undercutting the convex corners of the mask: {121} planes, which have very deeply textured surfaces, and {h12} planes, which form an octagon where they intersect with the mask. After a certain etch depth, the {111} planes disappear as the faster etching planes (etch rate >1.3 μm/min) initiated at the convex corners meet each other (FIG. 3 after 150 minutes). The needle shape is formed when the eight high index crystal planes, which are {312} planes, intersect on top of the frustum and come together at a single point, generating a sharp needle tip (FIG. 3 after 350 minutes in this example). At this stage, the remaining mask detaches from that microneedle.

Figure 4:
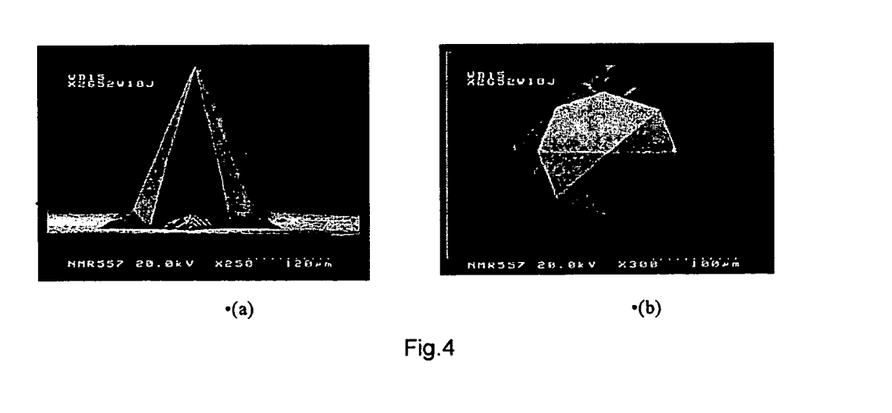
FIGS. 4(a) and 4(b) are SEM images of an end-product microneedle.

An example of a fully formed microneedle structure from such a process is shown in FIG. 4. The microneedle in this case is formed by high index {312} crystal planes and a small base of {121} crystal planes. The aspect ratio of needle height to inner bottom diameter of high index crystal planes is 3:2. There is a particularly smooth surface, which is highly advantageous for various applications, as discussed above.

Figure 5:
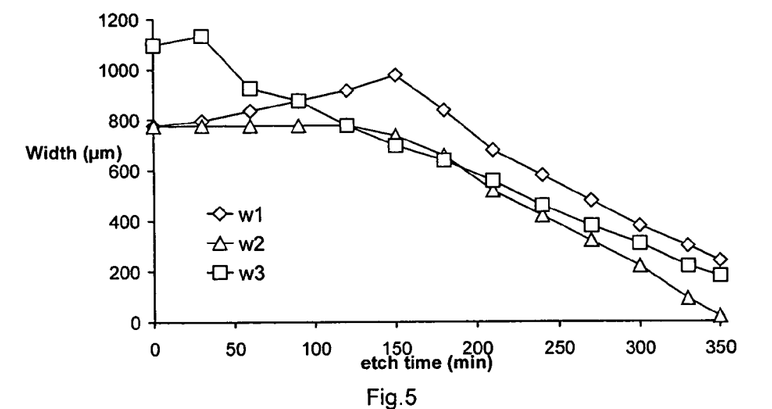
FIG. 5 is a set of plots of microneedle dimensions (from FIG. 2) against etch time.
Figure 6:
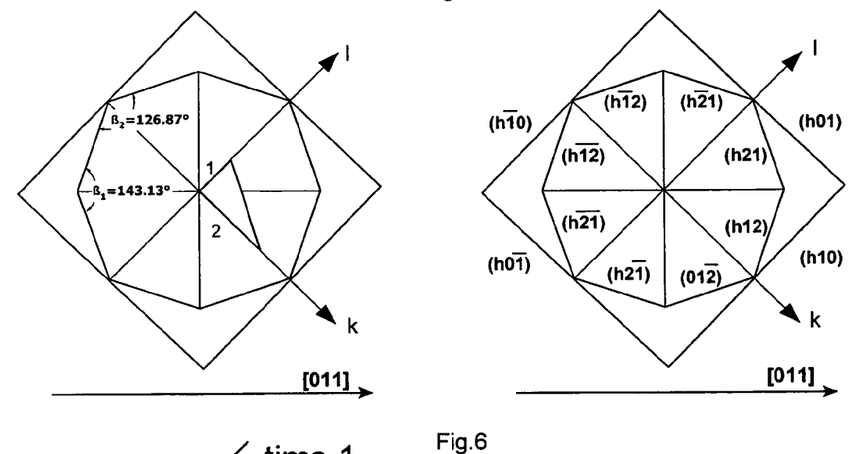
FIG. 6 is a pair of diagrams illustrating crystal planes and relevant nomenclature thereof.

Measured quantities of $w_1$, $w_2$ and $w_3$ are summarised in FIG. 5. In this example, the total etch time of 350 min corresponds to an etch depth of 307 µm. Measurements have shown that the diagonal length $w_3$ increases during the first 30 minutes of etching. The relatively stable {111} planes disappear as they are encroached by the {121} and {h12} planes which move laterally from the corners to the centre of the square. FIG. 6 depicts the various planes being discussed in this case. SEM measurements give an aspect ratio of height to width of the {h12} planes of approximately five; we therefore estimate that these high index planes have a Miller index of (512). It can be clearly seen that the {111} planes are removed between 120 and 150 minutes, when the dimensions $w_1$ and $w_2$ begin to decrease rather than increase. At this point the {h12} crystal planes now define the 3D etched structure. The base of the needle is a square, with edges oriented in [010] directions and is created by the conversion of {121} to {101} planes. The decrease of $w_1$ and $w_2$ is linear with time; however the slopes of the decrease of $w_1$ and $w_2$ are different. This indicates that the top width of the frustum decreases faster than the diagonal width of the bottom square.

Initially, it was assumed that an etch behaviour with a continuous etch of the same crystal planes existed during the entire etch time. However, the data supports behaviour where the high Miller index of the undercut planes change during etching, stabilising to a value of 3 at the conclusion of the process. Changes in the crystal plane indices explain the increase of lateral etch rates during the processing. This knowledge, i.e. awareness of these changes during the process, is very important for mask design and etch time determination. Once the {312} planes are established, they are stable during subsequent etching.

Etch Rate Determination

The following explains the calculations of etch rates in different directions, as a function of etch time and mask size. Herein, "mask" refers to the pad (for example square-shaped as previously mentioned) on the photolithography mask "assigned" to each microneedle. In other words, the photolithography mask, and subsequent nitride/oxide masking layers described above for the process description, is comprised of a series of such pads and under each such pad a microneedle will be formed by the etching process. These calculations are an important part of the process to prepare suitable photolithography masks for a process intended to fabricate microneedles of a desired needle height. All calculations refer to dimensions in microns (µm). FIG. 6 shows the crystal planes described in the text.

The etch depth $d_e$ over the etch time $t_e$ is equal to the etch rate in the [100] direction ($e_{r[100]}$). The average lateral etch rate in the [011] direction $e_{r[011]}(a)$ is given by the lateral etched distance on one side of the mask over the etch time:

$$e_{r[011]}(a) = \frac{m - w_2 - r_2}{2 \cdot t_e} \qquad (2)$$

The time-dependent etch rate in the [011] direction, given as reduction of half of $w_2$ over the etch time:

$$e_{r[011]}(t) = \frac{(w_{2(x)} - w_{2(x+t_i)})}{2 \cdot \Delta t_e} \qquad (3)$$

The lateral etch in the [011] direction starts after a delay of 120 min. Referring to FIG. 5, the width w2 starts to reduce after 120 min etching when the {111} crystal planes have been subsumed. The etch rate in the [010] direction (diagonal to the mask) varies non-linearly over time. The average lateral etch rate $e_{r[011]}$ increases linearly after that point. To calculate the lateral etch rates of the {h12} crystal planes from the beginning of the etch process, the diagonal length $w_3$ on the ground of the frustum in [010] direction has to be measured.

The etch rate $e_{r[010]}$ is then given by the difference of $\Delta w_3$ on one side of the square over the etch time:

$$e_{r[010]}(t) = \frac{(w_{3(x)} - w_{3(x+t_i)})}{2 \cdot \Delta t_e} \qquad (4)$$

Figure 7:
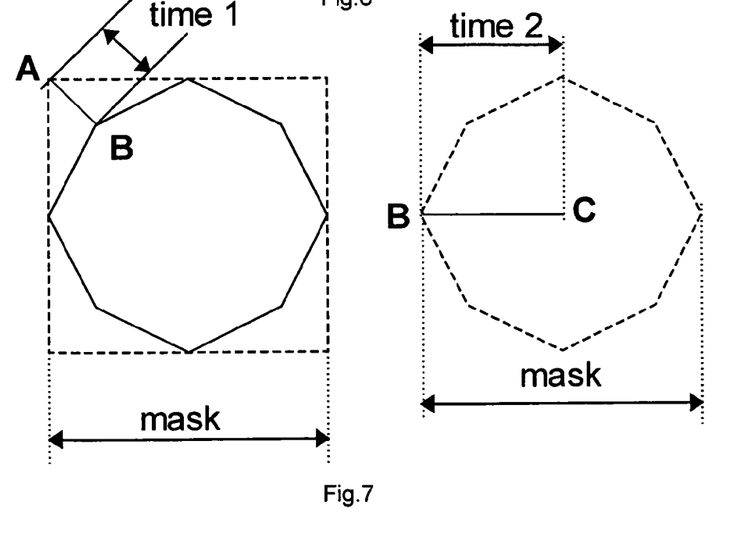
FIG. 7 shows the times $t_1$ and $t_2$ referred to in the detailed description of the etch process.

The etch times can be divided in two main parts, as illustrated in FIG. 7. The diagonal length of the frustum base increases during the first few minutes, due to etching of {111} crystal planes. Faster etching {121} and {h12} planes at the convex corner attack those crystal planes. After a while, {h12} planes form an octagon on top of the frustum. The Miller index h is very high, so that the angle α is nearly 90°. The diagonal length of the octagon is equal to the mask size, because two corners of the octagon fit to the mask length.

$$t_1 = \frac{(m+20) \cdot \sqrt{2} - m}{2 \cdot e_{r[010]}} \qquad (5)$$

After reaching this stage, we now look in the [011] direction to measure the time for the decrease of mask size. We can therefore integrate the mask reduction towards the needle formation. The neck between the microneedle and the mirrored needle on top is very close to breaking when $w_2$ is circa 20 µm wide.

$$t_2 = \frac{m + 20}{2 \cdot e_{r[011]}} \qquad (6)$$

The proportions of $t_1$ and $t_2$ depend on the needle height and therefore on the total etch time. The mask design size is than dependent on $t_2$ and $e_{r[011]}$ $$m = 2 \cdot t_2 \cdot e_{r[011]} + 20 \qquad (7)$$

Our process control software allows the endpoint time to be precisely identified, such that the endpoint is never over-shot. That is an important achievement of our process control methodology.

Figure 8:
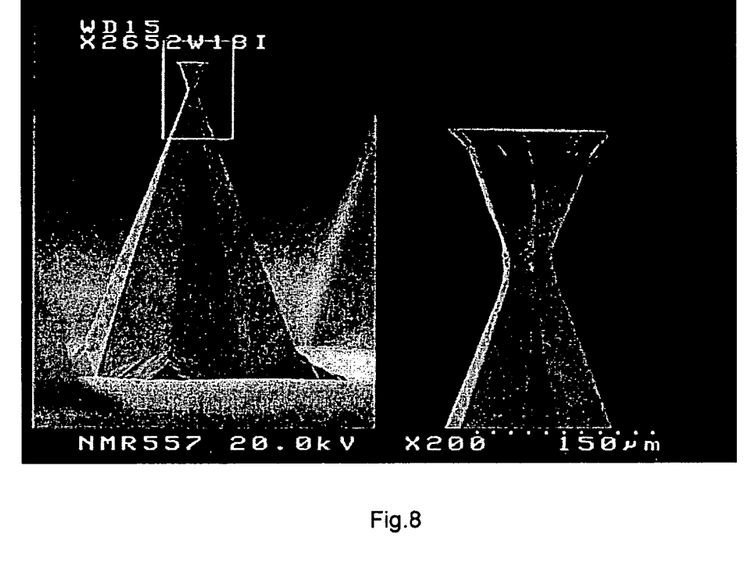
FIG. 8 is an SEM image of a microneedle tip just before completion of the etch process, in which an inverted microneedle at the tip is shown just prior to it breaking off to leave a sharp microneedle desired from the process.

Referring to FIG. 8, a negatively sloped inverted pyramid structure exists atop the desired microneedle. Measurements confirm that the negative slope region exists throughout the process. The height of this inverted needle is approximately 301 µm and the width of the top is approximately 20 µm, even for 150 µm and 300 µm tall needles. The inverted pyramid structure in FIG. 6 is separated when the 8 crystal planes form the needle tip. Water pressure for example can cause sufficient mechanical stress to result in a break of the inverted needle slightly earlier, just before reaching a sharp needle tip during etching. The ability to calculate this point is very advantageous. The software does this for any user for any bath conditions. Hence our process can accurately and reliably produce desired height microneedle arrays. Hence our process is reproducible.

Process Control System

The process control system is capable of accurately generating mask design rules for the wet etch fabrication process. Process control is on the basis that the needle fabrication etching process (stage 3) is actually a two-step process, with two clear etching sequences occurring. One will not start until the other has reached a critical point, which we have now identified and actually photographed.

The process control system ("NeedleSoft") allows accurate calculation of etch rates across the critical crystal planes and screen shots give plots of the etch rates as they happen. It also allows the operator to accurately predict the etch time endpoint at which sharp needles result. This is based on a simple requirement for the operator to make two key dimensional measurements (need to temporarily stop the etch run and make these two measurements) at a number of points (i.e. stop and measure twice, three times is better, though one stop has also delivered desired outcomes) near the end of the process. It is also possible to follow the two times $t_1$ and $t_2$ shown in the diagram in FIG. 7, which are the times for the two etch sequences.

The system may be easily adapted for different etch bath conditions, as they can be factored in at a calibration stage.

The system enables the designer to design masks for certain required needle geometries (height, shape, sharpness). This means that it can be used to make hillocks and frustums (non-sharp "needles") if so desired. One selects a needle height and the system generates the mask design parameters including pad size and gap between mask pads.

The system allows mask designers to build in compensation factors to the mask design, in the case where a researcher wishes to increase the needle density in a given area. In essence, inclusion of compensation factors are a known means of delaying the progress of alkaline etching processes at certain points on a mask or substrate structure. When this is applied to silicon microneedle array fabrication for example, it can deliver an increased needle density for a given chip size over that otherwise produced by the etching process. NeedleSoft removes the guesswork and trial and error. It allows the user to input a required needle density.

There is also a continuous and sometimes dramatic shift in crystal planes and in plane etch rate during the two main sequences of the etching stage of the process.

It will be appreciated that the process control system achieves the following:

Control of the silicon wet etching microneedle fabrication process.

The user can input a desired needle height, shape, sharpness, and density (within physical limits) and the tool outputs the mask design rules such as pad size and gap between pads.

It allows the user to calculate dimensions of mask compensation factors for cases where increased density is sought.

It can calculate etch rates across key crystal planes and allows the user to follow the etching process through its two main sequential stages.

It allows very precise prediction of etch time endpoint. The only user input at this stage is to make two key dimensional measurements at two or three time-points near the natural end of the etching process.

It is independent of bath composition.

Software to Control the Wet Etch Process

Figure 9:
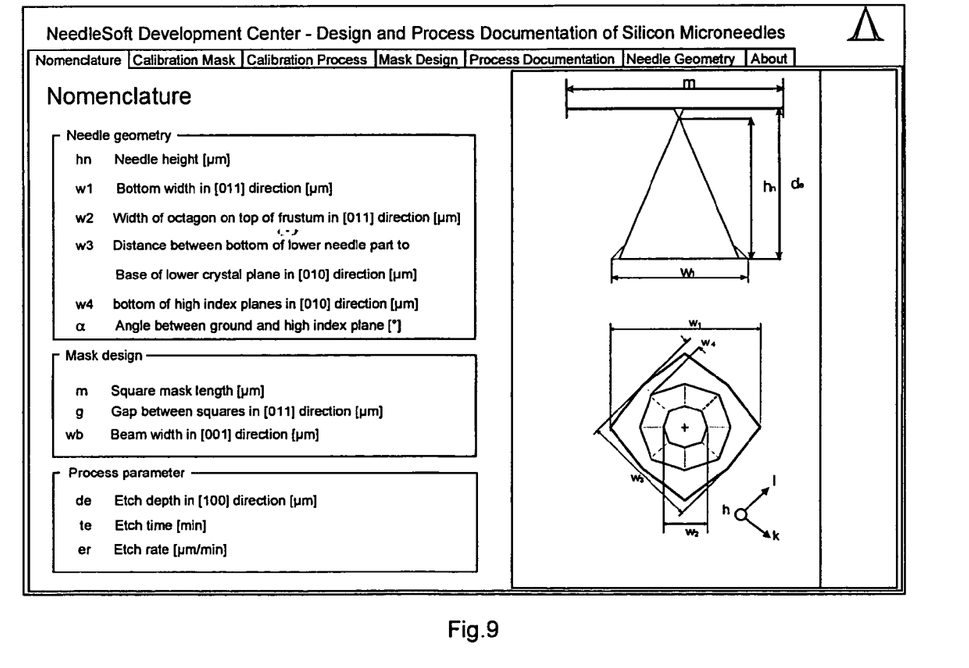
FIGS. 9 to 18 inclusive are GUI screen shots for a production controller showing the use of a "NeedleSoft" system for controlling the process.
Figure 10:
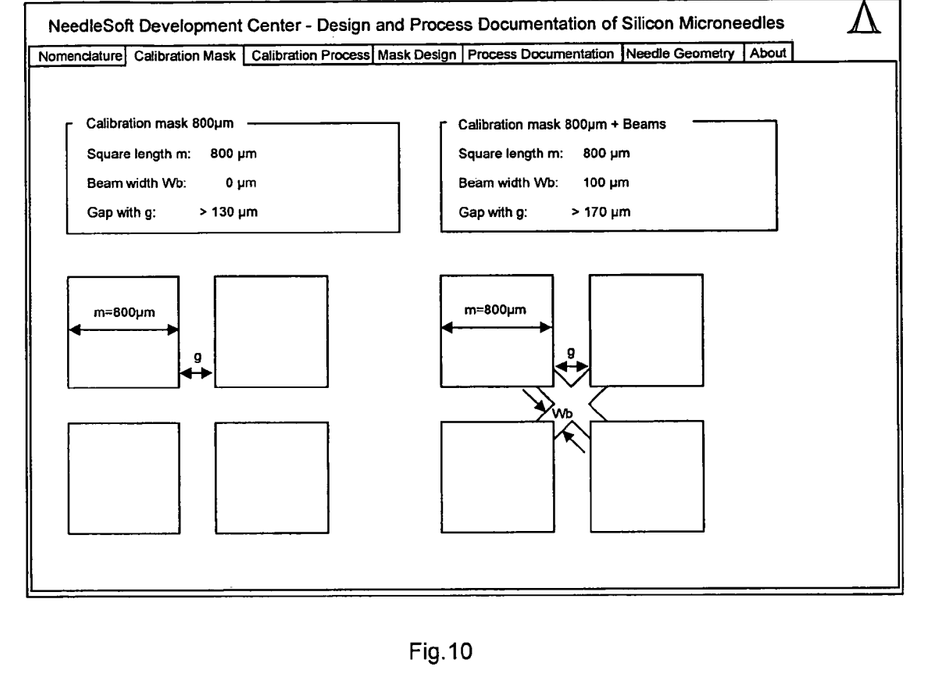
Figure 11:
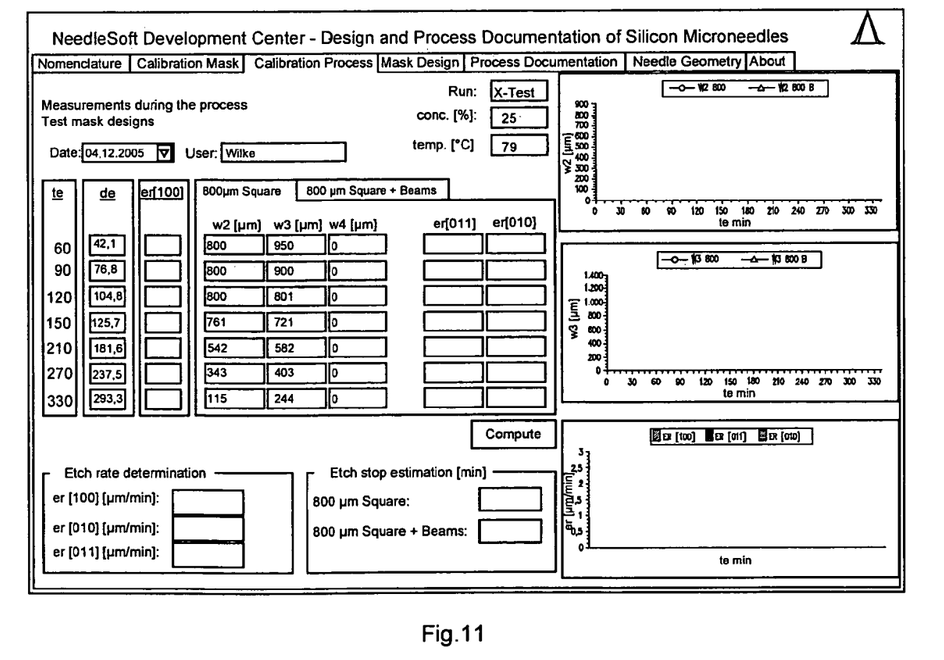

Various screenshots from the GUI of the NeedleSoft system are shown in FIGS. 9 to 18. These are explained below, for given examples. The software generates windows in the order of the development steps. The first window shows the nomenclature. The user needs to be familiar with the given abbreviations, which are used in the other windows. This is shown in FIG. 9.

The second window (FIG. 10) shows the calibration mask design. The software can be used for any KOH bath concentration and temperature. Therefore, it is necessary to first calibrate the process. The calibration process in the second window (FIG. 10) is based on the calibration design. If the user only needs the calibration of square masks, the modified mask design with beams to increase the needle density can be ignored.

During the calibration process (FIG. 11), the user has to measure the etch depth and make three geometry measurements taken from an overhead view of the top of a needle at the optical microscope. These are explained above and will be clear within the programme. Such measurements need to be inputted to NeedleSoft and saved. Of course, the monitoring steps may be automated using a machine vision measurement system.

Figure 12:
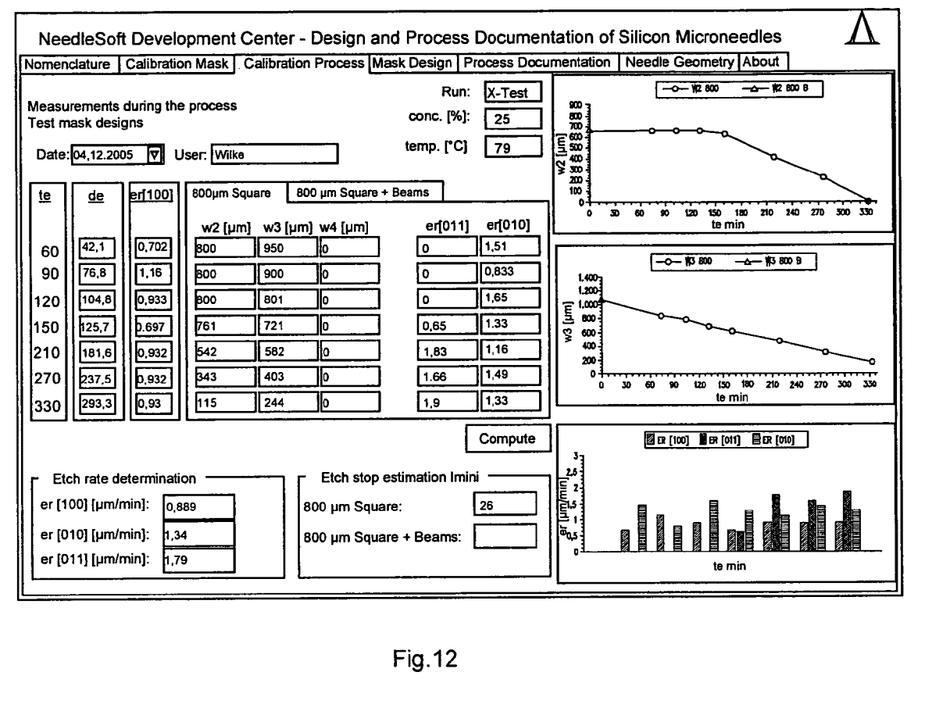

Pressing the "Compute" button (an example is shown in FIG. 12), etch rates in [011] and [010] direction are calculated for every etch interval. The average etch rates in three directions are shown at the left bottom side. Etch rate determinations are used to estimate the remaining etch time to get a sharp needle tip. The measurements can be documented for the square mask design, as well as for the square mask design with beams (see calibration mask). Three diagrams illustrate the documentation of the measurements for the width on top of the frustum ($w_2$) in [011]-direction and the diagonal width ($w_3$) at the bottom of the frustum in [010]-direction. Changes in the bath condition in terms of etch rates are shown in the third diagram (see FIG. 12). The etch rate in [100]-direction is normally constant. Changes during the process can cause changes of etch rates in other directions. Such changes will be highlighted by the software. Hence, collapse of the process due to unforeseen sudden changes in the etching conditions will be averted.

Figure 13:
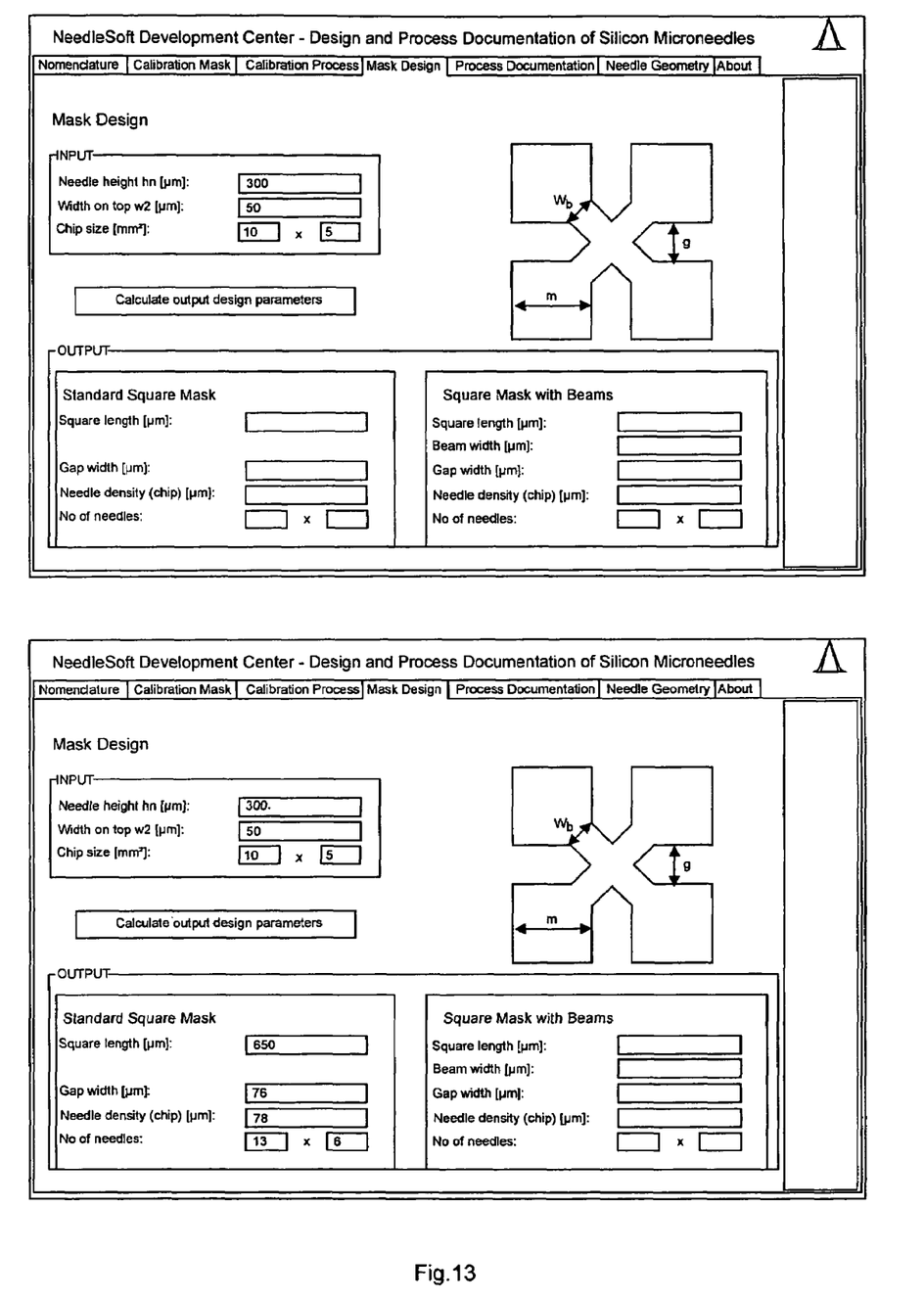

Loading the calibration file will automatically allow the calculation of the mask design parameters for that particular etch bath composition and conditions. These design options include: mask pad size, gap width between squares and needle density for a certain needle height, width on top of the frustum and chip size, as shown in FIG. 13.

Figure 14:
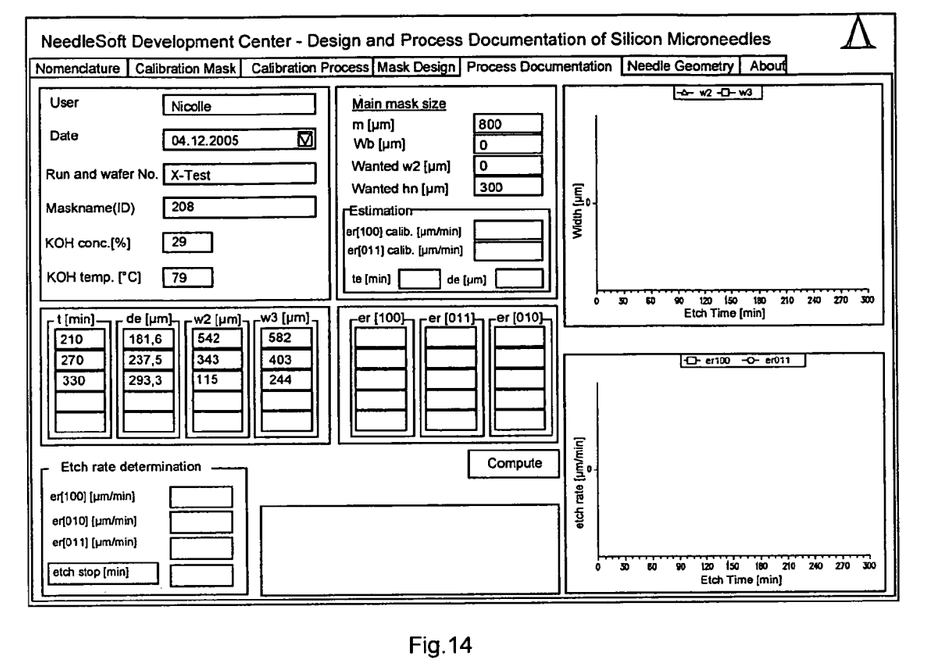
Figure 15:
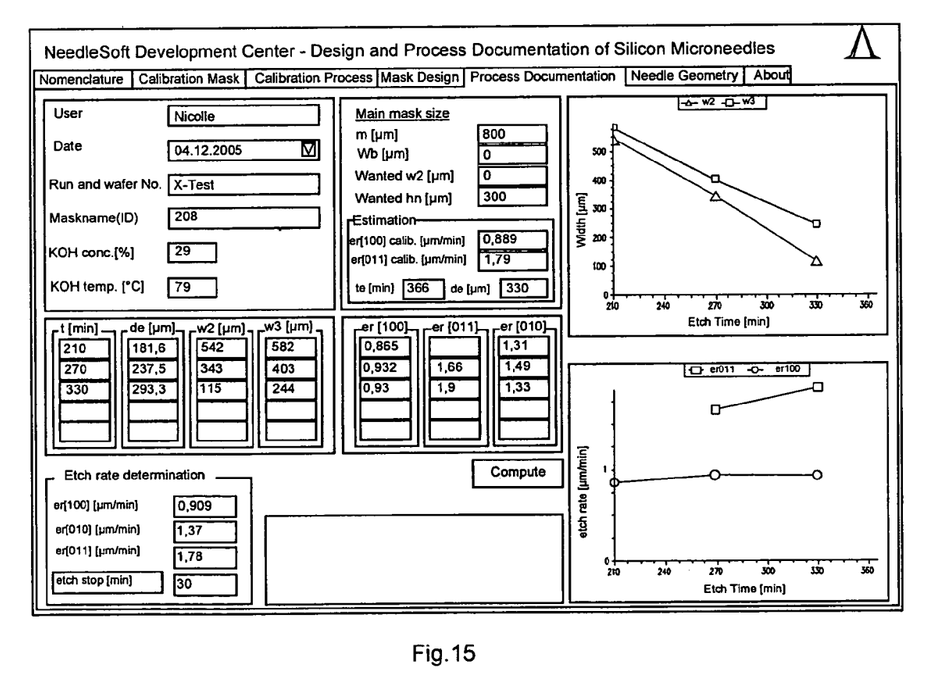

The mask design is now independent from the calibration. As shown in FIG. 14, the user enters the mask size being used in that case, the beam width (if using a modified mask design with such compensation factors included), the desired width on top of the microneedle (zero for a sharp needle) and the desired needle height. The calibration file has to be open to see the etch rates, but can also be entered manually. Pressing "Compute" calculates the etch rates for the etch intervals as well the average etch rates (FIG. 15). The user can also see the estimated remaining time to the conclusion of the process. The calculation of the etch stop takes into account the requirement to stop at a certain width on top. The diagrams show the development of $w_2$ and $w_3$ during etching and determination of the etch rate in [100] and [011]-directions.

Figure 16:
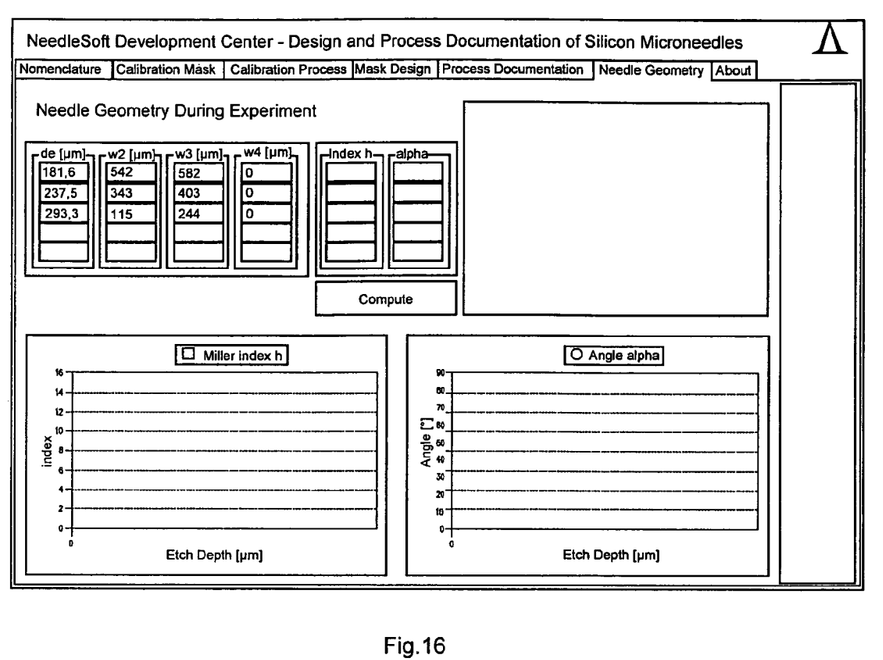
Figure 17:
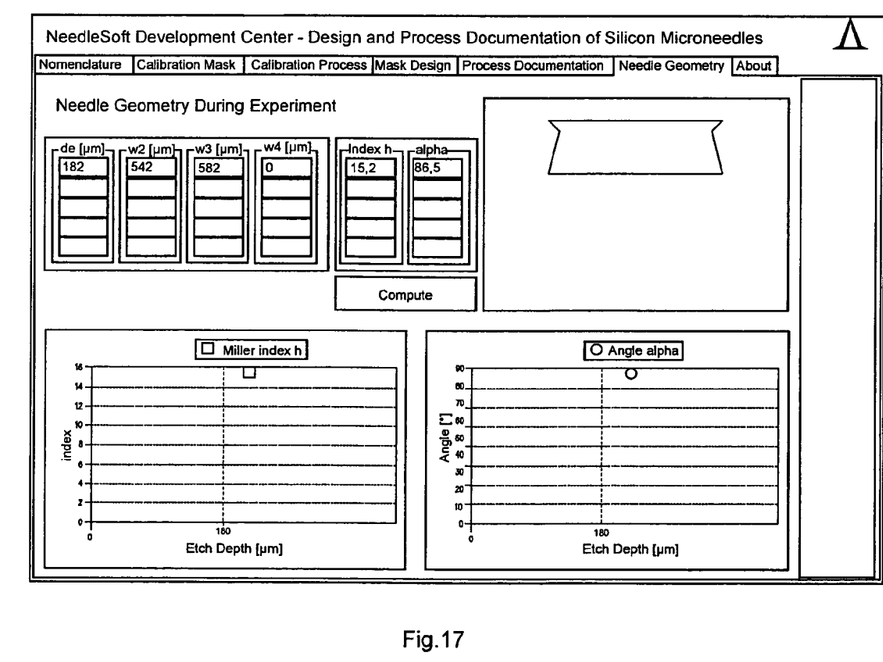
Figure 18:
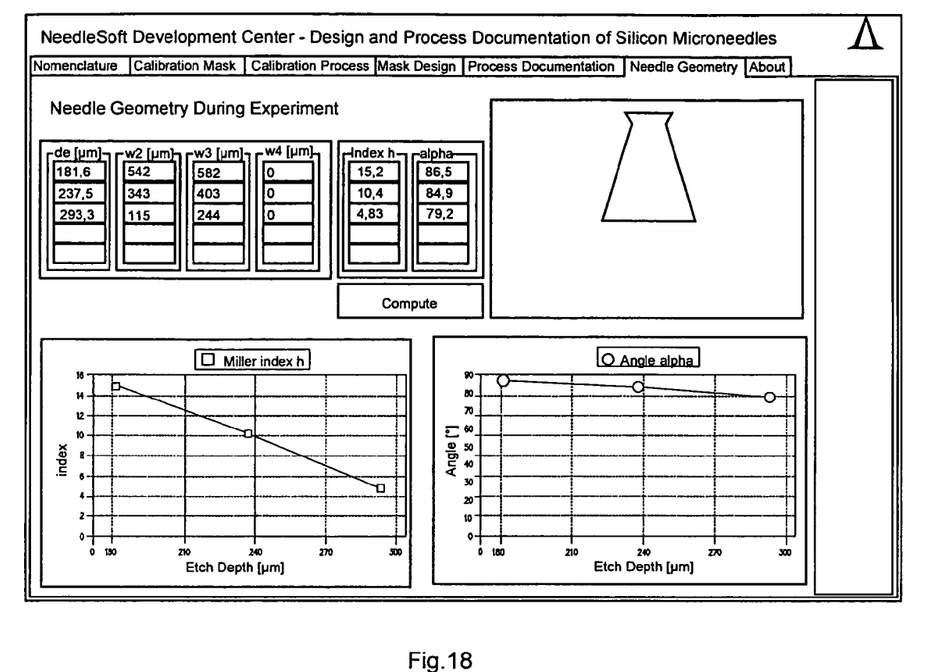

The needle geometry window can be used to "see" the actual needle geometry from a virtual side view. This gives a graphic depiction of how the etching is progressing towards the desired structural shape. Measurements are automatically entered into the input fields. For geometry determination, $w_4$ is measured and inputted as shown in FIG. 16. $W_4$ is normally less than 10 um. However, allowing the use of different etch parameters, this size can vary. The program calculates the Miller index "h" of the high index crystal planes and the angle α, FIGS. 17 and 18. The picture on the right side shows the estimated needle shape. Exact measurement requires SEM. The user can "see" the shape development after every etch interval, starting with a frustum shape until a sharp needle tip is achieved at the process endpoint.

Figure 19:
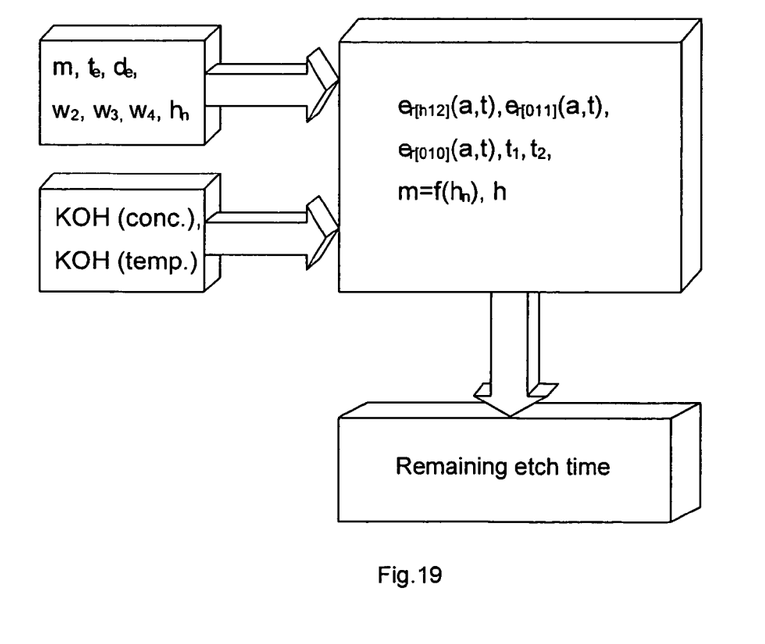
FIG. 19 summarizes input and output parameter of NeedleSoft.

FIG. 19 summarises all the process and measurement inputs required, the calculation background, and the important output parameters for and from NeedleSoft. The mathematical formulae executed by the source code, allow Needlesoft to calculate the etch rates in the important directions,
the etch times $t_1$ and $t_2$,
total etch time for any mask size,
the mask size for certain needle heights, and to provide a virtual representation of a side-view of a needle shape at any specified time point during the etch. On this foundation, Needlesoft can then be used during an etch process as was described above. As mentioned, the inputs to be measured when the process is stopped during the process control sequence are $w_2$, $w_3$, and $w_4$ (see FIG. 2), and the etch depth $d_e$. The output is an indication of the remaining etch time (in minutes) from that point onwards.

The invention is not limited to the embodiments described but may be varied in construction and detail.

The invention claimed is:

1. A process for manufacturing a microstructure needle article having a stem and a tip with a desired needle shape, the process comprising the steps of:
    providing a semiconductor bulk material,
    applying a mask to the bulk material, the mask having openings,
    exposing the pattern-masked bulk material to an hydroxide liquid etchant,
    allowing the hydroxide liquid etchant to enter the mask openings and to etch the bulk material until the desired needle shape is achieved, in which the needle tip is under, and pointing towards, the mask, and
    predicting remaining etch time by monitoring dimensions of the bulk material during etching, calculating actual etch rates in particular directions, and using said calculations to predict the remaining etch time until a stop time.

2. The process as claimed in claim 1, wherein the prediction step is performed to recognize a transition from one etching stage to a next etching stage.

3. The process as claimed in claim 1, wherein the prediction step is performed to recognize a transition from one etching stage to a next etching stage; and wherein etch rates for particular crystal planes for each stage are calculated.

4. The process as claimed in claim 1, wherein the prediction step comprises predicting:
    (a) a time $t_1$ for etching to a base of the needle; and
    (b) a time $t_2$ for etching to the tip of the needle.

5. The process as claimed in claim 1, wherein the prediction step includes taking measurements a plurality of times close to the end of the etching.

6. The process as claimed in claim 1, wherein the prediction step includes taking measurements a plurality of times close to the end of the etching; and wherein the etching is temporarily stopped while the monitoring takes place.

7. The process as claimed in claim 1, wherein the prediction step includes calculating a plurality of different etch rates.

8. The process as claimed in claim 1, wherein the prediction step includes predicting the stop time as being when bulk material crystal planes will intersect under the mask to form the needle tip.

9. The process as claimed in claim 1, wherein the prediction step includes predicting the stop time as being when the crystal planes will intersect under the mask to form the needle tip; and wherein the end point is when the mask will detach.

10. The process as claimed in claim 1, wherein the prediction step includes predicting the stop time as being when the crystal planes will intersect under the mask to form a point; and wherein eight planes intersect at the stop time.

11. The process as claimed in claim 1, wherein the prediction step includes predicting a stop time as being when crystal planes will intersect under the mask to form a point; and wherein the end point is when the mask will detach; and wherein eight planes intersect at the stop time.

12. The process as claimed in claim 1, wherein the prediction step includes predicting the stop time as being when crystal planes will intersect under the mask to form a point; and wherein eight planes intersect at the stop time.

13. The process as claimed in claim 1, wherein the prediction step includes predicting the stop time as being when crystal planes will intersect under the mask to form a point; and wherein the article base has {121} crystal planes.

14. The process as claimed in claim 1, wherein the prediction step includes predicting when certain crystal planes will be removed.

15. The process as claimed in claim 1, wherein the prediction step includes predicting different etching rates for different dimensions.

16. The process as claimed in claim 1, wherein the prediction step includes predicting different etching rates for different dimensions; and predicting a different etching rate in the top width of the needle frustum than diagonal width of the base.

17. The process as claimed in claim 1, wherein the prediction step includes predicting different etching rates for different dimensions; and predicting a different etching rate in the top width of the needle frustum than diagonal width of the base; and wherein the process simultaneously fabricates an array of upright out-of-plane needles.

18. The process as claimed in claim 1, wherein the prediction step includes predicting different reduction rates for different dimensions; and predicting a different etching rate in the top width of the needle frustum than diagonal width of the base; and wherein the process simultaneously fabricates an array of upright out-of-plane needles; and wherein the process simultaneously fabricates a plurality of arrays of needles.

19. The process as claimed in claim 1, wherein the prediction step is performed with only a subset of the arrays.

20. The process as claimed in claim 1, wherein the prediction step includes predicting different reduction rates for different dimensions; and predicting a different etching rate in the top width of the needle frustum than diagonal width of the base; and wherein the process simultaneously fabricates an array of upright out-of-plane needles; and wherein the process simultaneously fabricates a plurality of arrays of needles; and wherein the plurality of needles are fabricated on a semiconductor wafer.

21. The process as claimed in claim 1, wherein the prediction step includes predicting etch time according to predicted changes in crystal plane indices.

22. The process as claimed in claim 1, comprising a further step of automatically generating an etch mask design according to target needle parameters, etch parameters, and predicted etch rates.

23. The process as claimed in claim 1, comprising a further step of using the microstructure needle as a master to produce a plurality of microstructure needles in a polymer material.

24. The process as claimed in claim 1, comprising further steps of using the microstructure needle as a master to produce a plurality of microstructure needles in a polymer material; and wherein the semiconductor needle is used as a master in a mould.

25. The process as claimed in claim 1, comprising a further step of creating a hollow in the microstructure needle.

26. The process as claimed in claim 1, wherein the mask is of nitride material.

27. The process as claimed in claim 1, wherein the mask openings are formed by plasma etching.

28. The process as claimed in claim 1, wherein the etchant is potassium hydroxide.

29. The process as claimed in claim 1, wherein the etchant temperature is above 70° C.

30. The process as claimed in claim 1, wherein the etchant temperature is approximately 79° C. and the etchant is potassium hydroxide.

31. A process controller comprising a processor and an input interface, the input interface being for receiving process conditions and the processor being for performing the prediction step of claim 1.

32. A computer readable medium comprising software for performing the prediction step of claim 1 when executing on a digital processor.

* * * * *

UNITED STATES PATENT AND TRADEMARK OFFICE
CERTIFICATE OF CORRECTION

PATENT NO. : 7,651,946 B2
APPLICATION NO. : 11/637020
DATED : January 26, 2010
INVENTOR(S) : Wilke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 474 days.

Signed and Sealed this

Twenty-third Day of November, 2010

David J. Kappos
*Director of the United States Patent and Trademark Office*